United States Patent [19]

Sremac

[11] Patent Number: 4,562,432
[45] Date of Patent: Dec. 31, 1985

[54] VOICE OR BLOW-CONTROLLED SWITCHBOARD

[76] Inventor: Steve Sremac, 3549 Agate Dr., #8, Santa Clara, Calif. 95051

[21] Appl. No.: 409,621

[22] Filed: Aug. 19, 1982

[51] Int. Cl.⁴ .............................................. G09G 3/00
[52] U.S. Cl. .................................... 340/706; 340/802; 340/825.19; 381/110
[58] Field of Search ............... 340/711, 712, 706, 800, 340/802, 825.19, 286 M; 381/110

[56] References Cited

U.S. PATENT DOCUMENTS

| | | | |
|---|---|---|---|
| 3,651,512 | 3/1972 | Summers | 340/286 M |
| 3,806,911 | 4/1974 | Pripusich | 340/802 |
| 3,848,249 | 11/1974 | Meiri | 340/802 |
| 3,986,030 | 10/1976 | Teltscher | 340/802 |
| 4,081,623 | 3/1978 | Vogeley | 179/90 AN |

FOREIGN PATENT DOCUMENTS

WO83/00780 3/1983 PCT Int'l Appl. ............ 340/825.19

OTHER PUBLICATIONS

"Patient Breath Pulse Control System for Operating Various Electrical Devices", Western Electric Technical Digest, No. 54, Apr. 1979, R. P. Sapp, pp. 25-27.

Primary Examiner—Gerald L. Brigance

[57] ABSTRACT

This invention relates to voice or blow-controlled appliances. A single LED display digit continually flashes the digits zero through nine in succession, each number corresponding to an appliance. When a number flashes on this display digit, any word can be said or one can just blow into the microphone to turn on the appliance corresponding to that number. No physical contact is neccessary. An optional display-board can be used. An optional unique delay circuit may be used in cases where extremely high reliability is neccessary. The system can control up to ten appliances.

2 Claims, 7 Drawing Figures

VOICE OR BLOW-CONTROLLED SWITCHBOARD

BACKGROUND OF THE INVENTION

1. Technical Field

The present invention relates to voice or blow-controlled devices and is particularly directed to a novel voice-controlled switchboard which allows a handicapped person to control several appliances simultaneously.

2. Background Art

In the past, several types of environmental control systems have been employed. For example, a tongue-controlled environmental control system has been used specifically for handicapped people. The tongue-controlled system is disadvantageous because the person needs to stick out his tongue at the tongue-controlled switch every time he wants to turn an appliance on. Also, the handicapped person must move his eyes to follow the flashing of several rows of light-emitting diodes. Thus, it is somewhte inconvientient to use a tongue-controlled environmental control system.

In the past, voice-controlled environmental control systems have also been employed. These are disadvantageous because they use voice-recognition circuits. The system can fail in two ways. It may fail to recognize a word or mistake one word for another. Furthermore, it must be programmed for the individual user. Also, another type of voice-controlled circuit has been available. It is the reliable voice-controlled relay. It is disadvantageous because it can control only one appliance.

The principal object of the present invention is to provide a novel voice-controlled switchboard of simple construction which is free from the defects inherent in the prior art devices and which combines for the first time the digital electronics with the voice-controlled relay.

SUMMARY

More particularly, the present invention is predicated upon the concept of using the voice-controlled relay to generate a pulse, which is the input to the digital logic which controls the appliances. A digital display is utilized. A single LED display digit continually flashes the numbers zero through nine in succession, each number corresponding to an appliance. When a number flashes on the counter display, any word can be said into the microphone to turn on the appliance corresponding to that number. Because the microphone senses pressure, one can also just blow into the microphone. Any background noises have no effect on the reliability of the system. Normal talking, by the controller, will not effect the system because only a relatively loud word, directed towards the microphone and relatively close to it, will be recognized as a signal. By choosing to blow into the microphone, turning on an appliance becomes as easy as blowing out a candle. Drafty rooms will not affect system reliability.

An optical display-board can be used in addition to the single LED digit display. This display-board shows the current status of all the controlled appliances. There is one fixed digit for each controlled appliance. If a number is on, it means that the appliance corresponding to that number is on, and vice versa.

Specifically, the present invention uses the input pulse generated by the voice-controlled relay as an input signal. The system clock controls the counter which controls a BCD to decimal decoder. Each of the ten outputs of this decoder is fed into one input of its corresponding digital logic 2-input AND gate. There are ten of these AND gates. The other inputs of the AND gates are all tied together. The debounced signal from the voice-controlled relay is connected to the latter inputs.

Also, the BCD outputs of the same counter controls a 7-segment latch and driver which controls the flashing LED display digit.

Each of the ten AND gate outputs is connected to a separate flip-flop, each flip-flop controlling an appliance. In addition, there is an interface between each flip-flop output and the appliance it controls. Furthermore, each flip-flop is connected to function as a toggle switch.

So, the LED display continually flashes the digits one through nine in succession. When the handicapped person sees the number on the appliance that he wants to turn on flash on the display, he blows or says a word into the microphone and the input pulse is produced. Now, one input of each AND gate is at logic one state. Only one of these AND gates will have both of its inputs at logic one. It is the one which is connected to the decoder output which is currently at the logic one state. This is the number of the output corresponding to the number which is currently displayed on the single LED display digit. Because both inputs of this AND gate are at logic one, its output is also at logic one state. The zero to one transition at the AND gate output clocks a corresponding flip-flop which, in turn, controls the appliance.

These are many applications of the present invention. One of them is a voice-controlled elevator, with every floor number corresponding to a number on the single LED digit display. Also, there is the voice-controlled telephone where every number on the single LED digit display corresponds to a complete phone number. In that particular application, the present invention could be combined with the automatic dialing telephone presently available. Also, a potential applicaton is in voice-controlled military aircraft. In applications requiring extreme reliability, a specially designed delay circuit may be used.

One of the principal advantages of the present invention is that it is very reliable. It does not use voice-recognition circuits—just a voice-generated electrical pulse which enters the digital logic circuits. Consequently, it is also of much simpler construction.

Another advantage of the present invention is that it uses a single counting seven-segment display, with each number corresponding to an appliance. So, the user may just look at one digital display instead of rows of light-emitting diodes.

Still another advantage of the present invention is the ease of which it can be operated. A person can control any electrical or electrically controlled device without the need for any physical contact. Also, because it uses a digital display, no special codes need to be memorized in order to use the present invention.

These and other objectives and advantages of the present invention will be more readily apparent from a consideration of the following detailed description of the drawings illustrating a preferred embodiment of the invention.

BRIEF DESCRIPTION OF THE DRAWINGS
In the drawings.

DESCRIPTION OF THE PREFERRED EMBODIMENT

Figure 1:
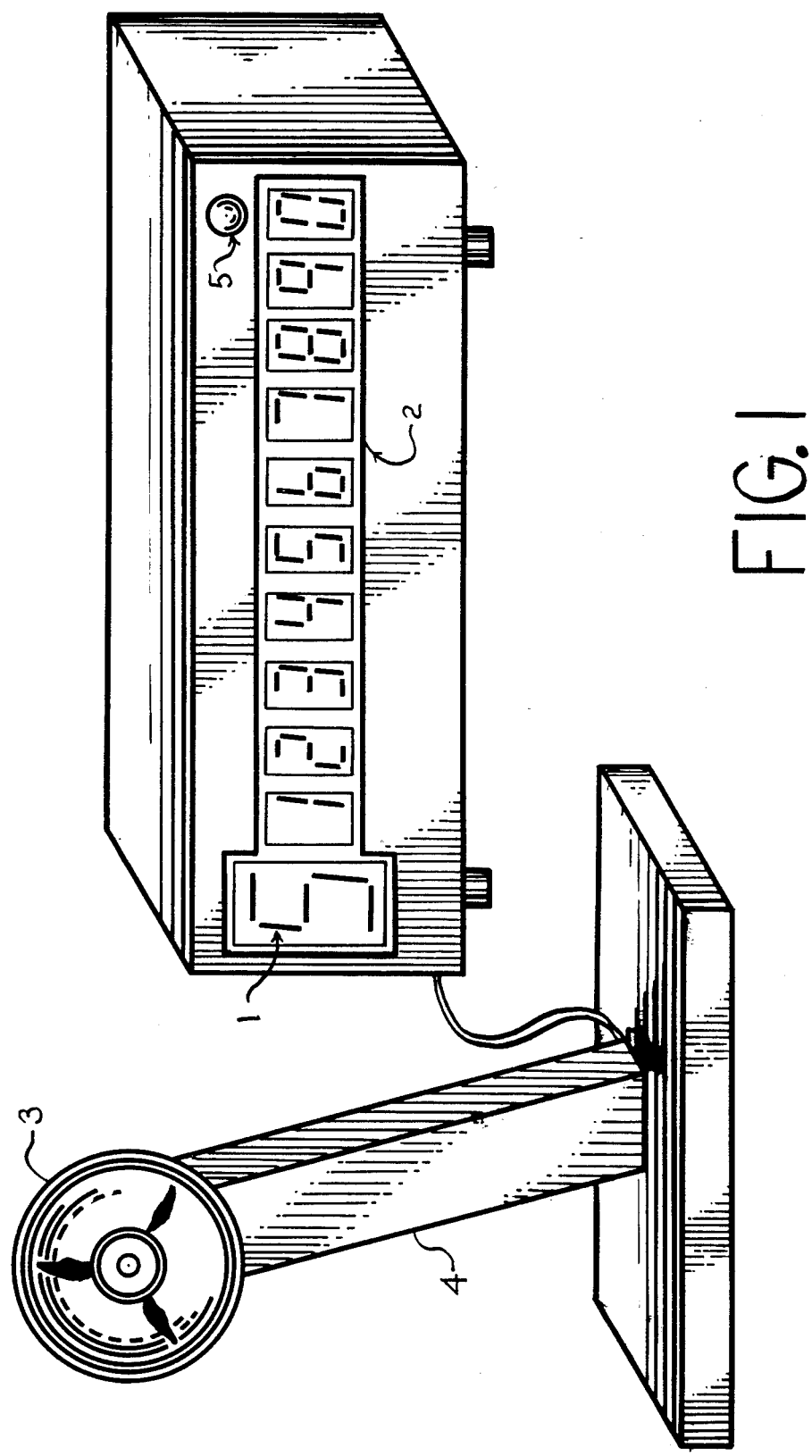
FIG. 1 is a front view of the voice or blow-controlled switchboard constructed in accordance with the principles of the present invention.

As shown in FIG. 1, the present invention comprises a single LED display digit (1) and the additional optional display-board digits (2). The single LED display digit continually flashes the numbers zero through nine in succession, each number corresponding to an appliance. When a number flashes on the single LED display digit, any word can be said into the "microphone" (3) to turn on the appliance corresponding to that number. The microphone, which is actually an 8 Ohm Impedance 22 Watt miniature speaker, is fastened to a stand (4). Also, there is an optional LED indicator (5) used in conjunction with the optional unique delay circuit. There is also a plug for each appliance on the back of this invention.

As shown in FIG. 1, the currently flashed number on the single LED display digit happens to be 5. If a word is now said into the microphone, the appliance that is hooked up to correspond to the number five will turn on. Also, the number 5 on the optional display-board will turn on, indicating that appliance 5 is on. Now suppose that you want to turn off appliance number 5, which is presently on. Again, when the number 5 flashes on the single LED display digit, you would blow into or say any word into the microphone. Then, the appliance and its corresponding number on the optional display-board would turn off. The optional display board shows the current status of all the controlled appliances. If a number is on, it indicates that the appliance corresponding to that number is on, and vice versa.

Figure 2:
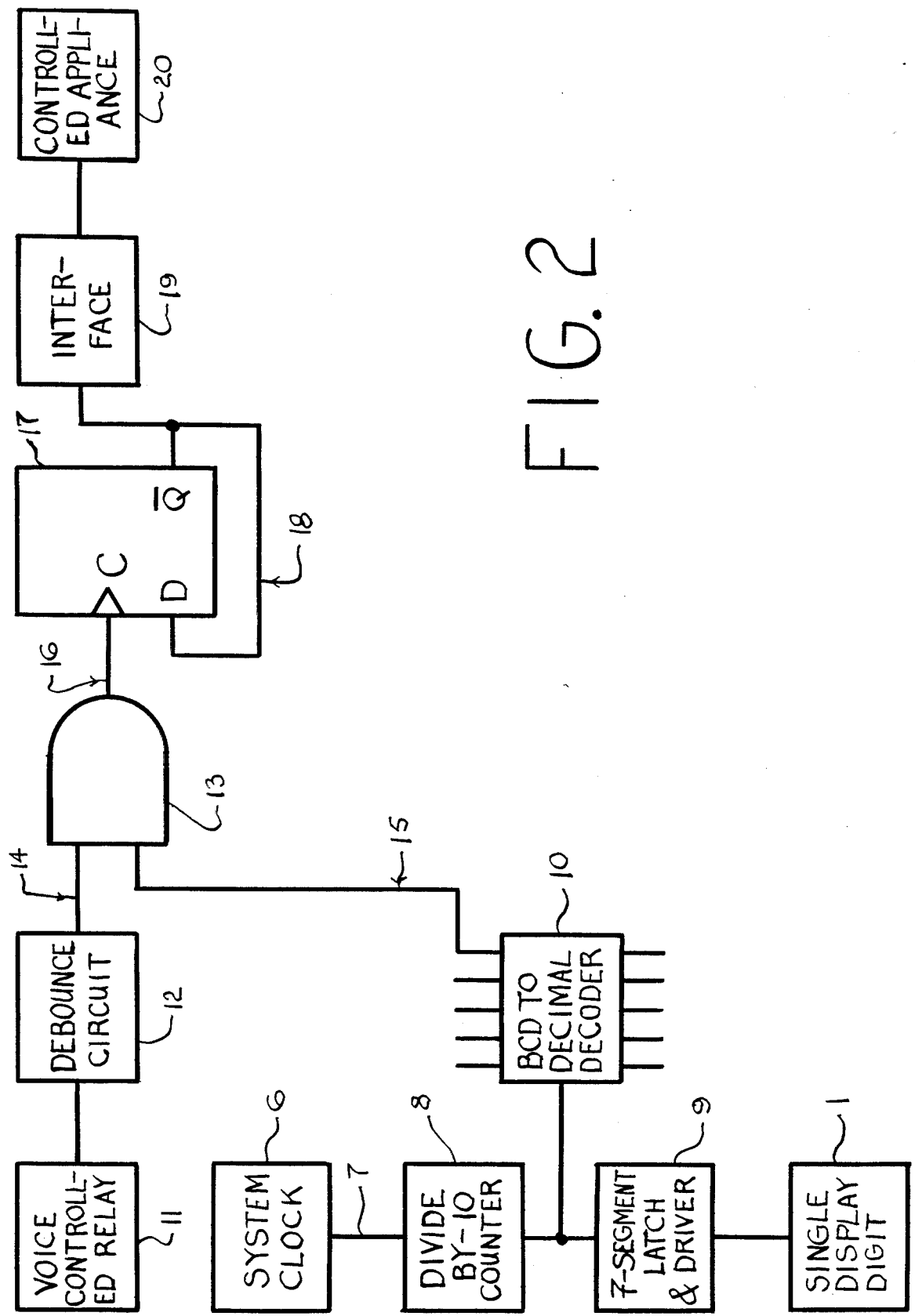
FIG. 2 is the flow diagram of the present invention showing the flow in detail for one of the controlled appliances.

As shown in FIG. 2, the output (7) of the system clock (6), which has a frequency of about one cycle per second, is fed into the divide-by-10 counter (8). The divide-by-10 counter produces a counting sequence in the bcd 1-2-4-8 output code. It counts only in the up direction. The outputs of the divide-by-10 counter are fed into the 7-segment latch and driver (9) which accepts the bcd input code and converts it to a 7-segment, high-current, positive-logic readout drive signal. The outputs of the 7-segment latch and driver are then connected to the single LED display digit (1) which counts in cycles from zero to nine, at approximately one-second per count.

The output of the divide-by-10 counter is also connected to the input of a BCD to decimal decoder (10) which decodes the binary-coded-decimal 4-bit code into 1-of-10 outputs.

When a word is said into the microphone, the voice-controlled relay circuit (11) generates an output pulse. The make sure that ony one pulse is admitted to the digital logic circuits, the output of the voice-controlled relay is connected to a debounce circuit (12).

The system clock, divide-by-ten counter, 7-segment latch and driver, single LED display digit, BCD to decimal decoder, voice-controlled relay, and debounce circuit are common to all ten controlled appliances.

There are ten outputs from the BCD to decimal decoder. Each of these outputs corresponds to a particular appliance. Each of the ten outputs of the BCD to decimal decoder is connected to an identical chain of circuits. The only thing in common to all of these ten independent chains is the debounce circuit output (14). Because these chains are all identical, the detailed drawing is shown for only one of the controlled appliances. In particular, appliance number five.

The output from the debounce circuit is connected to one input of each of ten 2-input AND gates, each AND gate corresponding to an appliance. Only one connection from the output of the debounce circuit is shown. It is the output that is connected to one of the inputs of the AND gate (13) that corresponds to appliance number five. The other input to this AND gate comes from the output (15) of the BCD to decimal decoder that corresponds to appliance number five. The output (16) of this particular AND gate is connected to the clock input of the corresponding D flip-flop (17). This flip-flop is connected to function as a toggle switch. This is done by feeding back the inverting output (18) of the flip-flop to its D input. The inverting output of the flip-flop controls an appliance (20) through an interface (19).

Suppose that the number five is presently flashed on the single display digit. The output of the BCD to decimal decoder which corresponds to the number five would presently be in the logic one state. If it is desired to turn on appliance number five, one must blow or say a word into the microphone during the approximately one-second duration of the pulse duration of the flash of the number five on the single display digit. Then, both inputs to the AND gate will be at logic one for the duration of the pulse generated by the voice-controlled relay circuit, which is a fraction of a second. Also, the output of the AND gate will make a logic zero to one transition, which will clock the flip-flop. Then, the flip-flop, which serves as the memory for the appliance number five, will change states and turn the appliance on, assuming that it was initially off.

Figure 3:
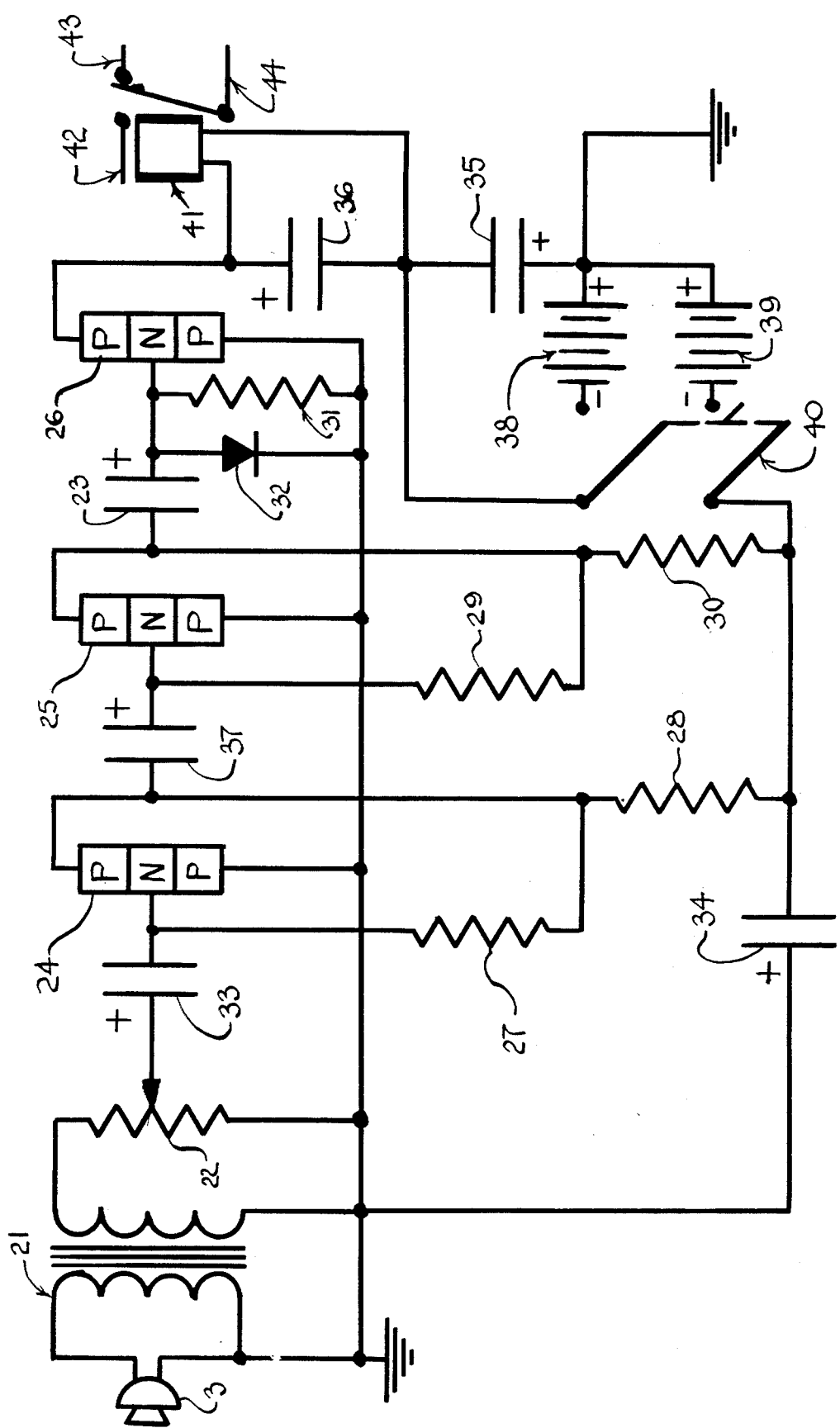
FIG. 3 shows the detailed drawing of the rectangular box labeled "voice-controlled relay" in FIG. 2.

FIG. 3 shows the modification of the voice-controlled relay circuit to serve as the input pulse to the digital logic. The microphone (3) is just an 8 Ohm impedance, 22 W, miniature speaker. The transformer (21) is connected in a different manner than the original voice-controlled relay specifies. Here, the 500 Ohm primary goes to the speaker, and the 3.2 Ohm secondary goes to the circuit, in connecting it. This will minimize the external, background noises from affecting the system. Although one has to say a word relatively loud, it is very easy just to blow into the microphone. The intensity of the blow is like blowing out a candle. The knob of the variable resistor (22) is turned fully counterclockwise, for maximum circuit response. The capacitor (23) is a 10 microFarad capacitor, used to produce a pulse of shortest nature, determined experimentally. The transistors (24), (25), and (26) are all PNP Ge transistors. AF Low Power. The resistors (27), (28), (29), (30), and (31) are 33, 4.7, 180, 10, and 22 kilo-Ohms respectively. The diode (32) is a GE axial-lead signal diode, AF/RF. Capacitors (33), (34), (35), (36), and (37) are 10, 10, 50, 100, and 10 microFarads, respectively. The D.C. power supplies (38) and (39) are 9 Volts each. The double pole switch (40) is normally in the closed position. The voice-controlled relay (41) is shown with its contacts (42), (43), and (44). These relay contacts are connected to the debounce circuit.

Figure 4:
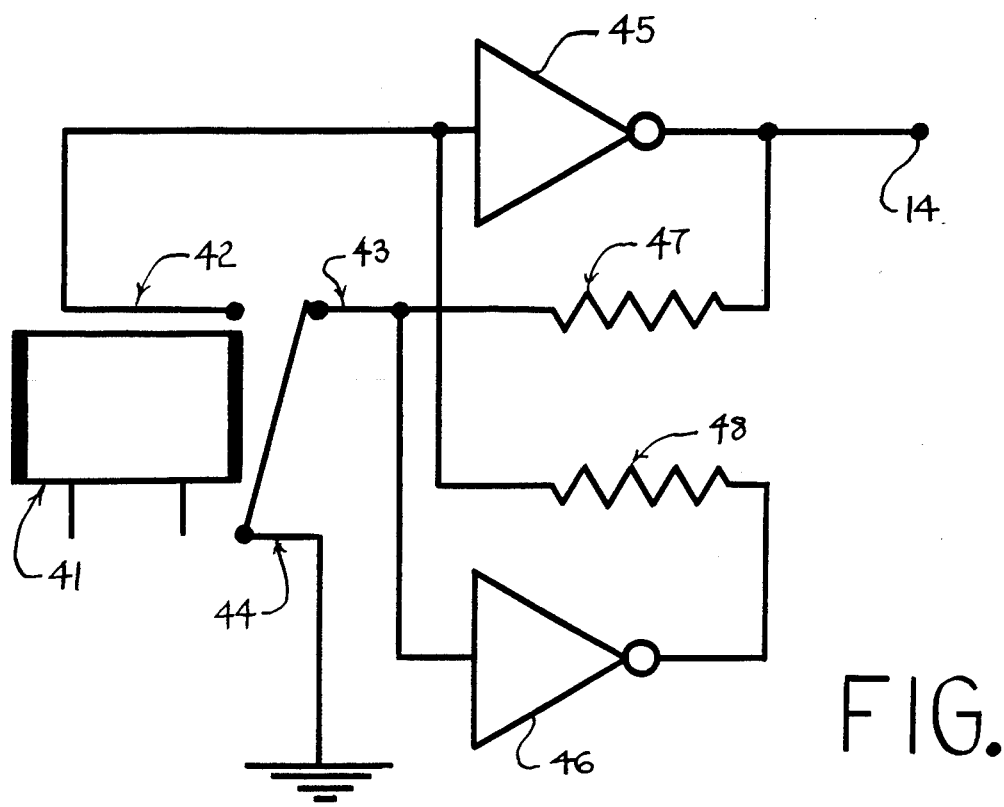
FIG. 4 shows the detailed drawing of the rectangular box labeled "debounce circuit" in FIG. 2.

The debounce circuit is shown in FIG. 4. The relay (41) is the same voice-controlled relay as shown in FIG. 3. The contacts of this relay (42), (43), and (44) are connected to the debounce circuit. This circuit consists of two inverters (45), and (46). These inverters use the same DC power supply as the digital logic in FIG. 2. Furthermore, contact (44) is grounded. Also, there are two 22 kilo-Ohms resistors (47) and (48). The noninverting output (14) is the output of the debounce circuit. This is the same output of the debounce circuit as shown in FIG. 2.

Figure 5:
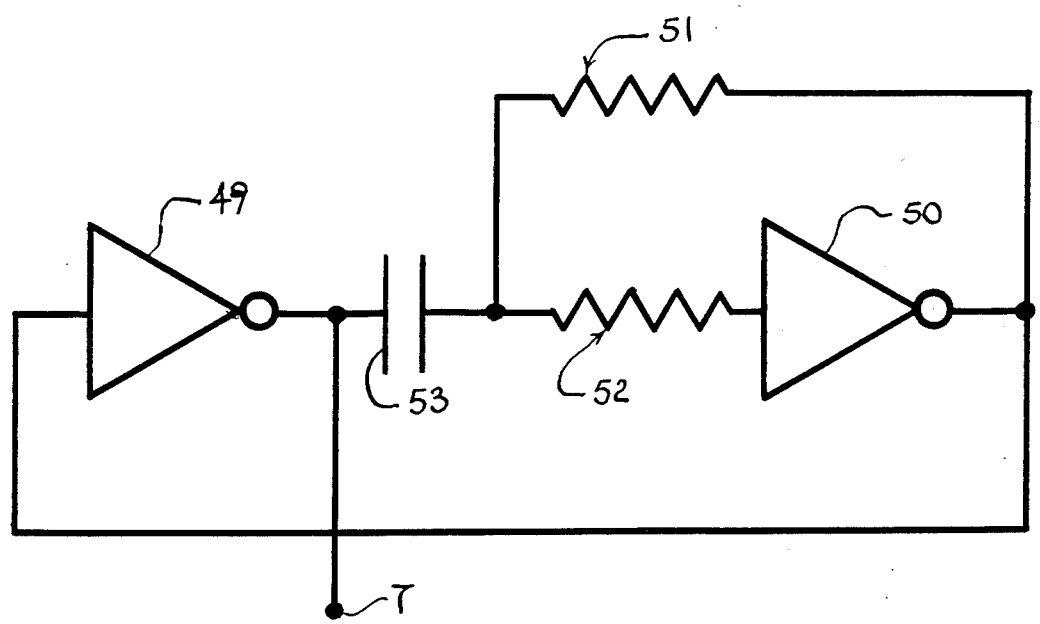
FIG. 5 shows the detailed drawing of the rectangular box labeled "system clock" in FIG. 2.

FIG. 5 shows the system clock. It is an astable oscillator. It consists of inverters (49) and (50); two resistors (51) and (52) 50 kilo-Ohm and 500 Ohms, respectively. The resistor (51) can also be a 50 kilo-Ohm rheostat. Also, there is a 10 microFarad capacitor (53). The output of the system clock (7) is the same output as shown in FIG. 2.

It has been found that the frequency of the astable oscillator output can be expressed by the following functional relation:

$$\text{frequency} = 1/2.2(R)(C)$$

where
R = value of resistor (52) in FIG. 5.
C = value of capacitor (53) in FIG. 5.

To get the frequency equal to one cycle per second, which is the desired pulse rate, a 50 kiloOhm resistor (52) and a 10 microFarad capacitor (53) were used. These values substituted in the functional relation give:

$$\text{frequency} = 1/2.2(50 \times 10^3)(10 \times 10^{-6}) \approx 0.91 \text{ cyc/sec}$$

which is approximately equal to a frequency of one cycle per second. A variable resistor in combination with a fixed capacitor could be used if a variable frequency, which is set by the rheostat, is wanted.

Figure 6:
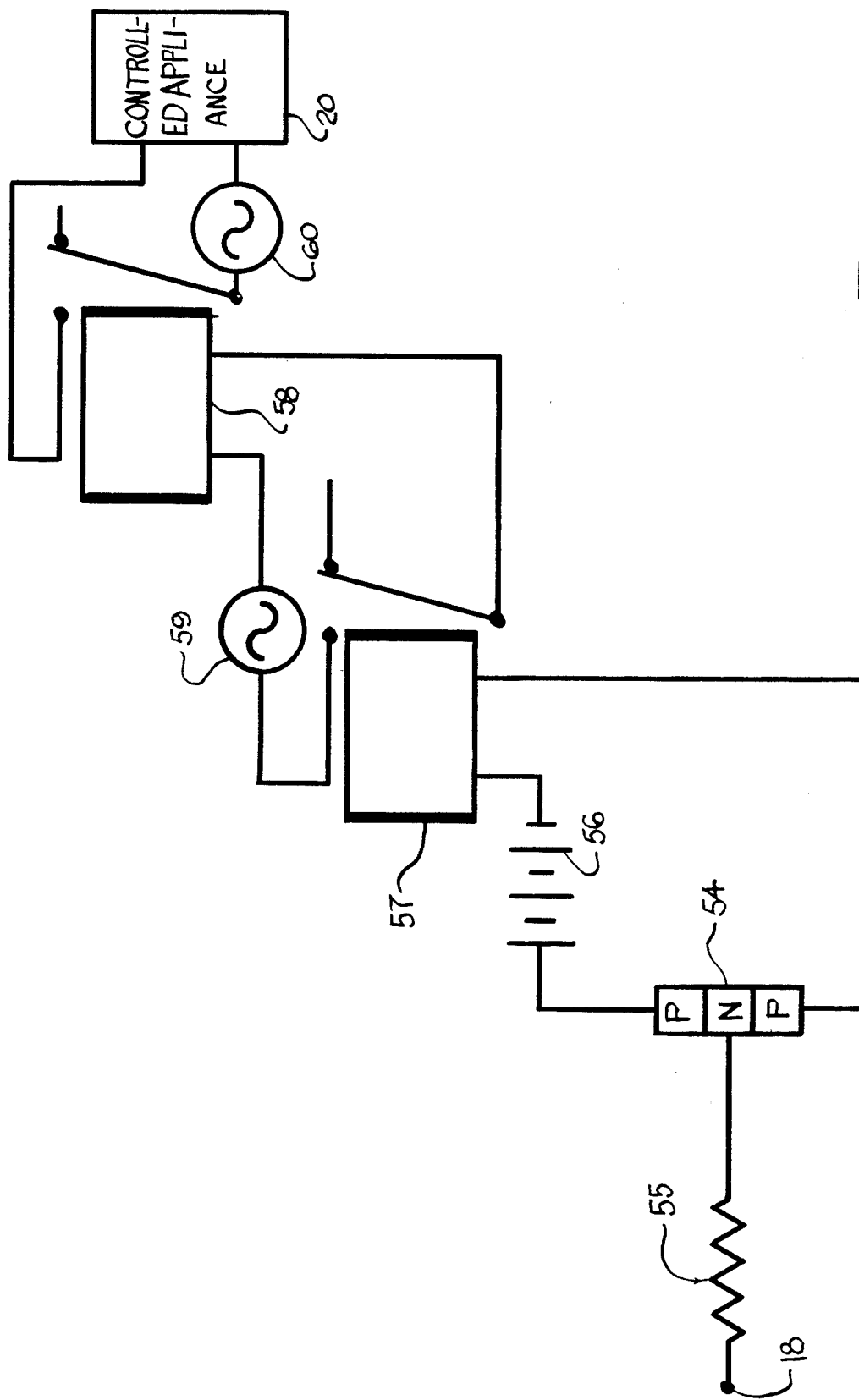
FIG. 6 shows the detailed drawing of the rectangular box labeled "interface" in FIG. 2.

FIG. 6 shows the interface for one of the ten controlled appliances. The input to the interface (18) comes from the inverting output of the D flip-flop that was shown in FIG. 2. Also shown in FIG. 6 is a general purpose PNP transistor switch and amplifier (54). The PNP transistor turns on when its input is at logic zero state. Also, there is a 220 Ohm current limiting resistor (55). The power supply (56) is the same power supply used for all of the digital logic circuits. The PNP transistor controls a D.C. relay (57). This relay will be on whenever the transistor is on. A D.C. appliance could be controlled by the contacts of the D.C. relay. The circuit would be closed whenever the relay is activated. However, for an A.C. appliance, the D.C. relay would have to be connected to an A.C. relay (58), as shown. However, an A.C. power supply (59) is needed to control the relay. This is separate from the A.C. power supply (60) needed to control the A.C. appliance (20). Because the relays use relatively little power, as compared with the appliances, the same A.C. power supply that controls this relay is connected directly to all ten of the controlled relays. Although SCR's may be used instead of relays, relays are recommended because the controlled appliance can't have any effect on the system.

Figure 7:
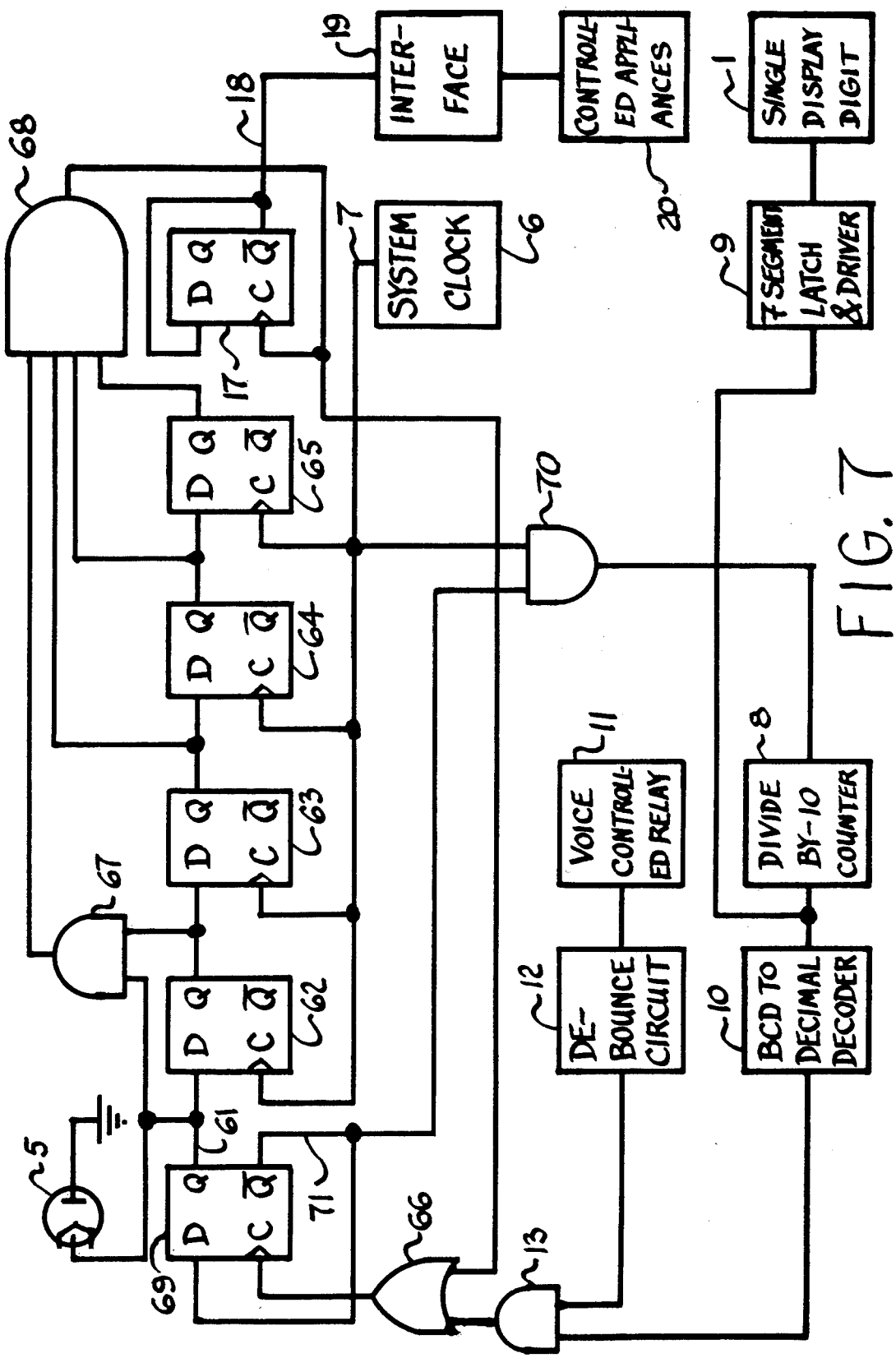
FIG. 7 shows the digital logic diagram of the optional unique delay circuit.

FIG. 7 shows the digital logic diagram of the optional unique delay circuit. The purpose of this circuit is to give extreme reliability in certain applications in which it is required. For example, if the controller inadvertantly made a loud cough directy into the microphone, one of the appliances might accidently get turned on if the system didn't utilize a delay circuit. With a delay circuit, however, if the person made a loud cough which was recognized as an input signal by the circuit, a red LED indicator (5) would turn on and the single LED display digit (1) will stop flashing numbers and remain at the current number. The corresponding appliance (20) will remain in its former state. About five seconds after the controller made the loud cough, the appliance corresponding to the number on the single digit display will turn on. Also, the counting sequence of the single LED display digit will continue. Now, if during that five second time interval, the controller wished to cancel the incorrect signal generated by his loud cough, all he had to do was to say a word into the microphone during that five second period to cancel that signal and the single LED display digit would continue in its counting sequence.

The delay is achieved by connecting a chain of D flip-flops with the non-inverting output of the preceding flip-flop connected to the D input of the succeeding flip-flop. The output (7) of the system clock (6), shown in FIG. 7, is connected to the clock inputs of the four D flip-flops (62), (63), (64), and (65) which are between the outer two. These four flip-flops may be readily implemented with a four-stage serial-in/parallel-out shift-register. The voice-controlled relay (11), the debounce circuit (12), the divide-by-10 counter (8), the 7-segment latch and driver (9), the single LED display digit (1), and one of the AND gates (13) corresponding to the number currently displayed on the single LED display digit are the same system components used in the system without the delay capability. The output of the AND gate is fed into one of the inputs of the 2-input OR gate (66), which, in turn, is connected to the clock input of the first D flip-flop (69) in the chain. The first and last flip-flop (17) in the chain are connected in the toggle manner. The outputs of all except the last must be fed into a six-input AND gate. This AND gate is implemented by cascading the two input AND gate (67) with the four-input AND gate (68). The output of the latter AND gate is connected to the clock input of the last flip-flop in the chain and also to the other input of the OR gate. The noninverting output (61) of the first flip-flop is connected to an LED indicator (5). The inverting output of the first flip-flop is connected to one of the inputs of another 2-input AND gate (70). The system clock input is fed into the other input of the latter AND gate. The output (18) of the last flip-flop controls the appliance (20) through an interface (19) as before. Note that there must be a separate delay circuit for each appliance being controlled. Although it is possible to implement this logic with elementary digital logic and flip-flops, it might be more economical to implement this logic with a PLA.

For an example of using this delay, suppose that it is desired to turn on appliance number five. When the number five flashes on the single LED display digit, one would blow into the microphone. The result would be that the output of the AND gate (13) would be in the logic one state for a short pulse. This clocks the first flip-flop in the chain, turning its non-inverting output into the logic one state. The inverting output would then be in the logic zero state. A logic zero would then be at one of the inputs to the AND gate (70). The output of this AND gate would then become logic zero, disabiling the divide-by-10 counter. So, the number presently on the single LED digit display would remain at the present number. No more clock pulses will be sent to the divide-by-10 counter until both inputs to the AND gate (70) will be at logic one again. So, the noninverting output of the first flip-flop will be at logic one. Also, the system clock is still controlling the four middle flip-flops. At the end of four clock pulses after the initial signal was given, all of the non-inverting outputs of the flip-flops (except the last) will be at logic one state. So, all of the inputs to the AND gate (68) will be at logic one, making its output change to logic one. This output pulse clocks the last flip-flop, which is the memory flip-flop of the controlled appliance. Also, it will turn one of the currently both logic zero inputs of the OR gate to the logic one state. The output of this OR gate will then change to logic one, which will clock-pulse the first flip-flop. Then, the inverting output of the first flip-flop will be at logic one state. This enables the AND gate (70), which, in turn enables the divide-by-10 counter, which allows the single LED display digit to continue in its counting sequence.

The appliance will change its state right after the output of the AND gate (68) turns into the logic one state.

Now, in the case where it is desired to cancel the signal, all that needs to be done is to say another word into the microphone before the last flip-flop in the sequence is clock-pulsed, namely before all of the inputs to the AND gate (68) are at logic one state. Then, one of the inputs to that AND gate will immediately turn to the logic zero state and within seconds, all of the noninverting outputs of the flip-flops will be in the logic zero state. However, you don't have to wait until five seconds have passed in order to use the switchboard again. As soon as you cancel the incorrect signal by blowing into the microphone, you can blow into it again to turn on the correct appliance without having to wait for any settling time.

The digital logic circuits desribed can be implemented in practically any logic family. However, it is preferred to use CMOS circuits because CMOS has a relatively large noise margin. Furthermore, with the use of CMOS digital logic gates, a large 500 microFarad, electrolytic capacitor is used to even further reduce the amount of affect that electrical noise has on the system.

Although a regulated D.C. power supply is not required for reliable circuit operation, it is recommended. In implenting the digital logic with CMOS, the AND gates are obtained from the 4081 chips. The divide-by-10 counter, the 7-segment latch and driver, and the BCD to decimal decoder can be obtained from the 4518, 4511, and 4028 CMOS chips, respectively. The D flip-flops are obtained from the 4013 chips. Also, a twelve volt D.C. power supply is preferred with the CMOS circuit implementation.

In constructing the invention, it is recommended that printed circuit boards be used to maximize compactability. Separate printed circuit boards should be used for the voice-controlled relay circuit and the digital logic circuits. The interface circuits should also be on a separate printed circuit board. The printed circuit boards are interconnected with wiring. The digital display board should also be on its own printed circuit board with the single LED display digit on the same board.

I am aware that details of construction may be varied and I, therefore, do not propose limiting the patent heron granted other than as indicated by the scope of the appended claims.

Having described my invention, I claim:

1. An apparatus for controlling electrical appliances by the use of an operator's breath, comprising:

a display means including a plurality of indicators, said indicators being sequentially enabled, one at a time, for a finite period, each said indicator corresponding to a particular appliance to be controlled, a switching means including a plurality of switches for selectively turning "ON" and "OFF" a corresponding plurality of appliances, said switching means being connected to said display means and being responsive to a single, breath operated switch such that, during the time an appliance indicator is enabled, a first actuation of said breath operated switch causes the switch corresponding to that appliance, after a predetermined delay, to reverse its "ON" or "OFF" state, and causes said display means to keep said enabled appliance indicator enabled during said predetermined delay, said switching means being further responsive to a second actuation of said breath operated switch during said predetermined delay, to prevent the reversal of said corresponding switch and to cause said display means to resume said sequential enablement of said appliance indicators.

2. An apparatus for controlling electrical appliances by the use of an operator's breath as in claim 1, further comprising:

additional indicators for indicating the "ON" or "OFF" state of the appliance corresponding to the enabled one of said plurality of indicators.

* * * * *